United States Patent
Mitsuda et al.

[11] Patent Number: 6,013,024
[45] Date of Patent: Jan. 11, 2000

[54] HYBRID OPERATION SYSTEM

[75] Inventors: Miyuki Mitsuda; Masahide Kimura, both of Shizuoka, Japan

[73] Assignee: Suzuki Motor Corporation, Shizuoka, Japan

[21] Appl. No.: 09/009,328

[22] Filed: Jan. 20, 1998

[30] Foreign Application Priority Data

Jan. 20, 1997 [JP] Japan .................................. 9-020976

[51] Int. Cl.[7] .......................... A61B 1/005; A61M 37/00
[52] U.S. Cl. ............................. 600/146; 600/149; 604/95
[58] Field of Search .................................. 600/146, 147, 600/149, 150, 151, 109; 604/280, 95

[56] References Cited

U.S. PATENT DOCUMENTS

| | | | |
|---|---|---|---|
| 4,011,872 | 3/1977 | Komiya | 607/7 |
| 4,836,187 | 6/1989 | Iwakoshi | 600/158 |
| 4,995,396 | 2/1991 | Inaba | 600/109 |
| 5,293,872 | 3/1994 | Alfano | 607/7 |
| 5,400,769 | 3/1995 | Tanii | 600/152 |
| 5,411,527 | 5/1995 | Alt | 607/120 |
| 5,438,975 | 8/1995 | Miyagi | 600/146 |
| 5,467,767 | 11/1995 | Alfano | 607/88 |
| 5,520,222 | 5/1996 | Chikama | 600/146 |
| 5,549,542 | 8/1996 | Kovalcheck | 600/146 |
| 5,619,993 | 4/1997 | Lee | 600/146 |
| 5,704,898 | 1/1998 | Kokish | 600/146 |
| 5,733,245 | 3/1998 | Kawano | 600/146 |
| 5,762,609 | 6/1998 | Benaron | 600/473 |
| 5,810,715 | 9/1998 | Moriyama | 600/146 |

*Primary Examiner*—John P. Leubecker
*Attorney, Agent, or Firm*—Jones Volentine, LLP

[57] ABSTRACT

A hybrid operation system that manipulates an object with the tip of a conduit inserted into said object comprising a conduit having inside multiple tubes that are inserted into the object, a driving mechanism that drives the multiple tubes, an analysis mechanism that analyses the condition of the object sensed by the tip of the conduit, a display that displays the analysis results of the analysis mechanism, and an input mechanism that outputs to the driving mechanism commands for operating the multiple tubes in response to the manipulation of the operator. The ends of the multiple tubes are detachably mounted on the driving mechanism and the input mechanism. In the field of medical treatment, examinations are performed with one probe for the initial examinee. Then, when the examination of the initial examinee is completed, the probe is detached from the system main body at the connecting members. The detached probe is disposed of, and a new probe is attached to the system main body by the connecting members for examination of the next examinee. Thus, examination is performed hygienically and rapidly.

7 Claims, 17 Drawing Sheets

FIG.3

| FUNCTION BLOCKS | DESCRIPTION |
|---|---|
| A, B) | INTERNAL OBSERVATION BY INTRODUCTION OF AN OPTICAL FIBER |
| C) | MEDICAL TREATMENT OF INTERNAL AND EXTERNAL TISSUES BY LASER IRRADIATION |
| D) | PHOTOCHEMICAL REACTION EXAMINATION AND MEDICAL TREATMENT BY LASER IRRADIATION |
| F) | CLEANING, STERILIZATION, AND SUPPLY OF LIQUID MEDICINE INTERNALLY, EXTERNALLY, AND TO THE TIP SURFACE OF THE PROBE |
| E) | SUCTION OF DISPOSED MATERIALS AND CRUSHED MATERIALS AND DISCHARGE OF WASTE FLUID |
| G) | BENDING, MOVING, OR TILTING THE SURFACE OF THE TIP OF THE PROBE |
| H) | INTERNAL EXAMINATION WITH ULTRASOUND WAVES, AND EXAMINATION BY SPECTROPHOTOSCOPE |
| I) | MEDICAL TREATMENT ON INTERNAL AND EXTERNAL TISSUES AND ELECTROPORATION BY ELECTRODE |

HYBRID OPERATION SYSTEM

BACKGROUND OF THE INVENTION

1. Field of the Invention

The present invention relates to a hybrid operation system (an optical fiber scope), in particular to a hybrid operation system used in the field of medical treatment for such things as photochemical treatment, picture image diagnostics, laser treatment, ultrasound treatment, and non-invasive diagnostics, and in the field of industry as such things as a narrow probe, or a micro machine.

2. Background and Material Information

Conventionally, the following type of device was used as a hybrid operation system. With the current advanced medical technology, lesions are discovered on an observation screen while observing with an optical fiber scope. When necessary, the lesions are cut out while mechanically invading the tissues with minute forceps or the like, inserted through a cavity (a lumen or tube) built inside the optical fiber scope.

For example, in an examination performed by a doctor using a stomach camera, an optical fiber scope probe is inserted through the patient=s mouth. Even if the tissue in the picture image taken by the optical fiber scope appears to be normal at a glance, when a tissue culture is done there may be cells abnormally proliferating. These can be seen as a cancerous reserve army of cells, and further investigational procedures follow. However, with an optical fiber scope for medical treatment already in clinical use, the width and length is set to match the appropriate region such as the upper digestive organs like the stomach, for lower digestive organs such as the rectum and the colon, for gynecological uses, for the urinary organs, for the respiratory organs, and for blood vessels such as veins and arteries, and the type can be subdivided according to the specific diseased body.

Such things as internal inspection after attaching a communication cable through a narrow pipe, observation of the internal condition and maintenance inspection of all types of storage tanks, internal inspections of electronic equipment after assembly or during use, breakdown inspections, and maintenance inspections for all types of plumbing equipment, are examples of the industrial uses of an optical fiber scope.

However, with the conventional optical fiber scopes above, the following inconveniences arose because they are all one unit from the objective lens through the main body of the optical fiber scope to the portion where it is manually operated. In other words, in all types of devices used in medical treatment, bacteria could adhere to the surface during examination of a patient. Yet current optical fiber scopes are expensive, and discarding such devices would raise the cost of the examination. Therefore, the probe (the lead-in portion inserted) is sterilized and used again for the next examination. However, it is preferable to use disposable devices as much as possible in order to prevent secondary infection to other people.

Also, aside from such necessary constructional elements as the light guide which transmits light and the image guide which transmits an image, a cavity (a lumen) into which forceps or washing fluid are introduced is housed inside the optical fiber scope. In this case, the diameter of the optical fiber scope itself becomes larger, and if such forceps or the cavity are not constructed inside symmetrical to the central axis of the optical fiber scope, distortions are created easily depending on the direction of the bend.

Further, in order to grant a degree of freedom to the direction of the tip of the optical fiber scope, a wire rod with a certain degree of rigidity, such as a metallic wire, is inserted in the main body of the optical fiber scope. Thus, the operator (at this stage the clinical doctor), controls the X and Y axis direction of the tip of the optical fiber scope by operating the multiple dials on the handpiece of the optical fiber scope with one hand. At the same time, while inserting the tip of the optical fiber scope with the other hand into the affected area, the operator proceeds by advancing the scope farther inside little by little while looking at the picture image screen obtained.

This method demands a long period of time until the operator becomes practiced in the use, because a high degree of skill is necessary for such things as dexterity of the fingertips, and powers of concentration.

Further, the areas observed with the optical fiber scope are pathological areas relating to a wide range of specialties such as internal medicine, urology, gynecology, respiratory and circulatory medicine, and surgery. Scopes of all shapes have been disseminated as devices for each specialty, but the techniques of usage differ for each, and one can not use a common device for all areas. Because of this as well, a long period of time is necessary for the operator to become practiced in the use.

Further, the optical fiber scope for industrial use differs from that for medical use, requiring longer durability because it is used under harsh environmental conditions. As a result, in many cases a corrosion resistant metallic material is used such as inflexible stainless steel. Therefore, the inconvenience arises that it is not suited to observation inside bent or twisted piping.

SUMMARY OF THE INVENTION

The purpose of the present invention is to overcome the inconveniences of the conventional devices, and in particular to provide an improved hybrid operation system which can be used commonly in multiple specialties.

Another purpose of the present invention is to provide a hybrid operation system with increased reliability of its influence on the examination results and the object of the examination without allowing the special properties of the object of each examination to influence the object of other examinations, regardless of whether it is used in humans, animals, or for industrial purposes.

A further purpose of the present invention is to simply and in a short period of time prevent infection during examination when the object of examination is a human or an animal.

Another purpose of the present invention is to expand the range of examination of the probe, even more so than when multiple fibers and lumen are built inside the probe in advance in order to allow common use across multiple specialties.

The purpose of the present invention is further to provide a device for performing surgical treatment without making an incision in the affected area of the patient. Also, to provide a device for performing gene manipulation of cells in the living body of an animal rather than in a culture.

Thus, the hybrid operation system which manipulates the object with the tip of the conduit inserted into the object comprises a conduit having multiple tubes inside that enter the object, a driving mechanism that drives the multiple tubes, an analysis mechanism which analyzes the condition of the object detected by the tip of the conduit, a display which displays the analysis results of the analysis mechanism, and an input mechanism which outputs commands for moving the multiple tubes to the driving mechanism in response to the manipulation of the operator. The driving mechanism and the analysis mechanism are detachably mounted at the rear end of the multiple tubes.

In the field of medical treatment and the like, examination is performed on the first examinee with the first probe. Then, when the examination of the first examinee is completed, the probe is detached from the main body of the system at the connecting elements. The detached probe is disposed of, and a new probe is connected to the main body of the system with connecting elements for the examination of the next examinee. In this way, examinations are performed hygienically and rapidly.

Another embodiment of the present invention where the object is manipulated by the tip of the conduit inserted in the object, comprises multiple tubes that enter the object, a conduit enclosing the multiple tubes with sides made from polymeric material, a driving mechanism that drives the multiple tubes, an analysis mechanism that analyzes the condition of the object detected with the tip of the conduit, a display that displays analysis results from the analysis mechanism, an input mechanism which outputs commands for moving the multiple tubes to the driving mechanism in response to operator manipulation, a bending portion which bends along with the multiple tubes positioned on the tip of the conduit, operation wires which pass around the outer periphery of the conduit from the tip of the bending portion to the rear end of the bending portion, and which pass through the inner periphery of the conduit from the rear end of the bending portion to the end of the conduit, and a tip driving mechanism that adjusts the tension of the operation wires in order to bend the bending portion.

The range of examination of the object can be expanded because the bending portion bends. In particular, because the operation wires bend the tip by pulling it from the outer side of the bending portion, even when the conduit encloses multiple tubes in order to provide multiple functions and becomes quite fat, the device can be bent satisfactorily.

BRIEF DESCRIPTION OF DRAWINGS

FIG. 3 is a chart showing a list of the functions in the field of medical treatment for the construction shown in FIG. 2.

DETAILED DESCRIPTION OF THE PREFERRED EMBODIMENTS

Figure 1:
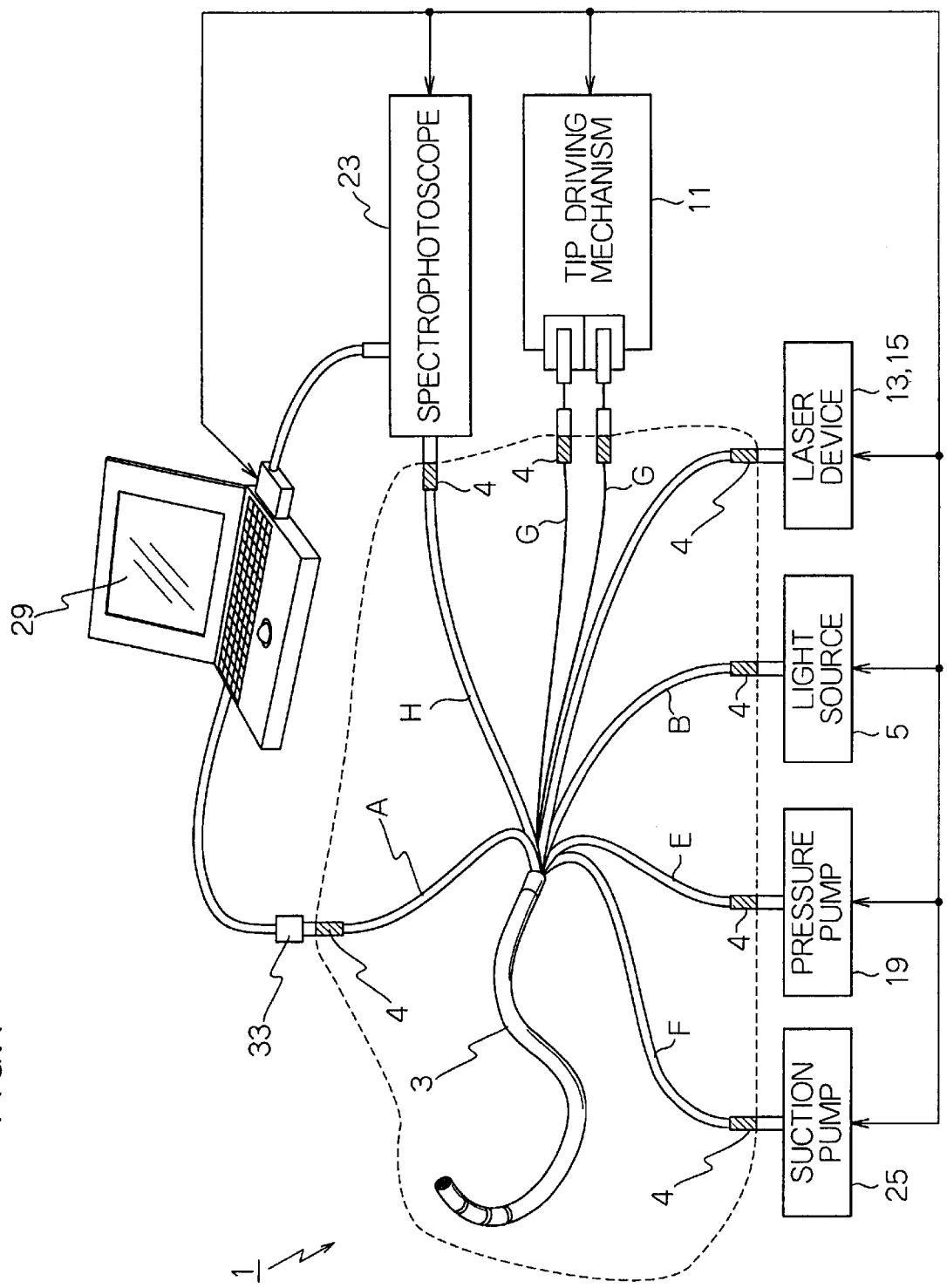
FIG. 1 is an explanatory view of an embodiment of the present invention.

Referring to FIG. 1, the hybrid operation system 1 is equipped with a conduit (probe) 3 enclosing internally multiple tubes A-H, and a driving mechanism and an analysis mechanism connected to the multiple tubes. The driving mechanism is equipped with a suction unit having a suction pump 25 that suctions the object for all types of examination from the tip of the probe 3, a supply unit having a pressure pump 19 for injecting fluid into the object, a light source 5 for irradiating the object at the tip of the probe 3, and laser devices 13 and 15 to irradiate the object with laser light. The driving mechanism is connected to a control computer (PC) 29, which is a part of the driving mechanism.

The analysis mechanism is equipped with a CCD camera 33 and a photoelectric conversion element that converts light received at the tip of the conduit 3 to photoelectricity, a spectrophotoscope 23 that detects the strength of the light for each wavelength, and a PC 29 for analysis that analyzes the signal output from the CCD camera 33 and the spectrophotoscope 23. The PC 29 performs such functions as spectrum analysis, picture image processing, and control of all driving mechanisms according to the control program stored in advance. A logic circuit created according to control logic can be used instead of PC 29.

In the example shown in FIG. 1, the tip of probe 3 is bendable due to joints 3b. This increases the objects which can be examined and manipulated with the probe 3 inserted inside. Each tube enclosed in probe 3 is connected to the driving mechanism by plastic pushpull FC connectors, connection members 4, corresponding to the nature of the tube.

For medical treatment, the conduit is inserted into the body in the same way as is that which is widely known conventionally as a stomach camera, and the length is set so that the tip reaches close to the affected area. The preferable length for medical treatment if the entire length of the conduit is 50 cm, is 10 cm–1 m depending on the use. The probe 3 can be inserted into such regions as the upper digestive system, the lower digestive system, the respiratory system, the organ system in gynecology, or the urinary organ system, and also in the eye, the ear and nose, cerebral blood vessels, coronary blood vessels, and the abdominal organs.

When using for experiments and research in such areas as gene manipulation within the live body of animals, the length is adjusted to correspond for example to the animal=s digestive system. For industrial use, the length is set to correspond to any use to inspect and repair the inside of all types of piping.

Figure 2:
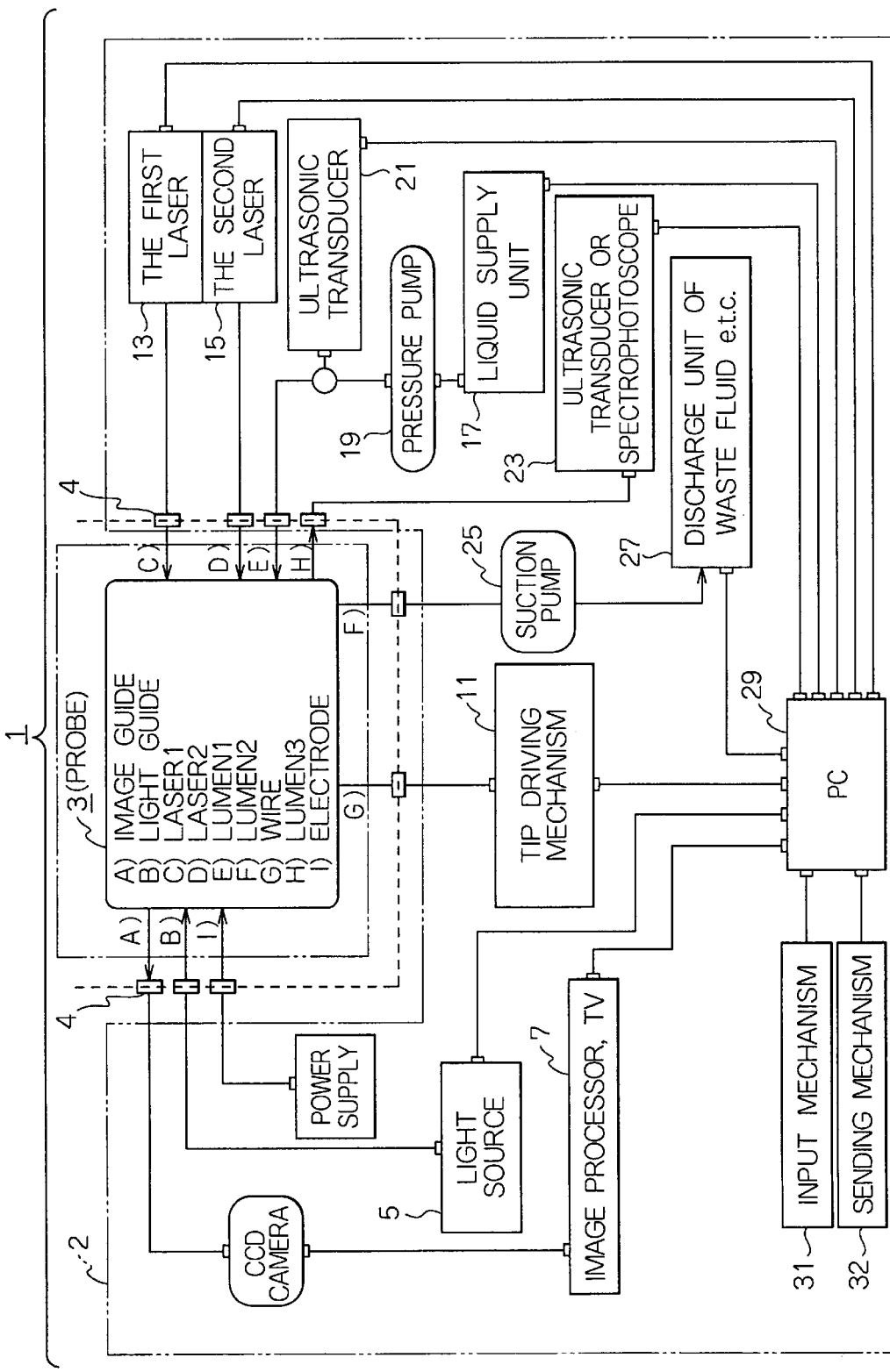
FIG. 2 is an explanatory view of the details of the construction shown in FIG. 1.

Referring to FIG. 2 for further detail, system 1 is equipped with tubes (A)–(I). The image guide (A) is an optical fiber that receives light at the tip of the probe 3 inserted into the object, and transmits this received light to the CCD camera 33. The light guide (B) is also an optical fiber that transmits light output by the light source 5 to the tip of the probe 3 to irradiate the surroundings of the tip of the probe 3.

Laser 1 (C) is a fiber that incidents laser light and transmits the laser light output from the first laser 13 to the tip of the probe 3. Laser 2 (D) similarly transmits laser light output from the second laser 15 to the tip of the probe 3. In the field of medical treatment, one laser is a laser for the medical treatment of the affected area where the tip of the probe is inserted, and the other laser is for photochemical reaction. Two lasers can also be used in conjunction even for industrial purposes when lasers of differing strength are necessary. If using a semiconductor laser device that can dynamically change its strength as lasers 13 and 14, optical fibers C and D can be made only one fiber. For industrial use, the laser can be used to cut or heat the object. Lumen 1 (E) is a hollow tube, and is used to inject liquid into an object close to the tip of the probe 3. Lumen 2 (F) is used to suction liquid from the object to the driving mechanism.

The present system is also furnished with operation wires G for bending the tip of the probe 3. By sending the operation wires out or winding them back up, the tip of the probe is bent in both directions. Lumen 3 (H) inserts a transmission member that transmits ultrasound waves, for example. Lumen 3 (H) can also be used for photo analysis by passing an optical fiber through it. Electrode (I) discharges applied voltage from the power source at the tip of probe 3. For industrial use, it can be used for welding the object.

Tubes (A)–(I) are connected to the driving mechanism depending on their role. In order to detach probe 3, they may also be connected by connectors 4. General optical fiber photo connectors are used for connecting optical fibers A, B, C, and D. Couplers may also be used for connectors 4 in such cases as when the picture image photographed by CCD camera 33 is processed in parallel by two types of image processors with different purposes, or when the sequence of laser light sources 13 and 15 is switched.

In the example shown in FIG. 2, an ultrasonic transducer 21 is used connected to the pressure pump in order to perform injection smoothly by oscillating the liquid when injecting. In the example shown in FIG. 1, an optical fiber is inserted into the hollow of lumen 3 (H) and connected to spectrophotoscope 23, but in the example shown in FIG. 2, an ultrasonic wave transmitter is inserted in the hollow of lumen 3 (H) in order to get an ultrasonic image of the object by transmitting ultrasonic waves with ultrasonic transducer 21. In this way, lumens can be used for a variety of uses other than injecting or suctioning liquid.

The tip driving mechanism 11 is attached to PC 29. This tip driving mechanism 11 causes the tip of the probe to bend by sending out operation wires G and pulling them back in. Sending mechanism 32 is also connected to PC 29. Sending mechanism 32, along with the tip driving mechanism 11, also sends out and pulls back in probe 3. By mechanically introducing probe 3 into the object, operation is made easy and minute control is possible as compared to manual operation.

A white halogen lamp is used as the light source 5 connected to the light guide (B). The power source 40 connected to electrode (I) supplies electricity at a set voltage determined in advance. Depending on the use of this system and the electrode, a transformer to switch the voltage of the power source can be connected to power source 40 so that a change in voltage can be set by computer from PC 29.

We have shown an example in which an image processor and a TV (display) are connected directly to the CCD camera 33, but image processing can also be performed by PC29 with the picture image output from PC29 to the TV. For example, if the field of vision is broadened by changing the size of the picture image with input mechanism 31, or by mounting a convex lens on the tip of the image guide (A), image processing can also be done by the PC 29 in such cases as when the display of the picture image as is is switched to a picture image wherein the curved image is converted to a flat image.

Referring to FIG. 3, the following is a list of functions (A)–(I) corresponding to tubes (A)–(I) when the hybrid operation system of the present invention is applied to the fields of medical treatment and biochemistry research.

(A,B) Internal observation by introduction of an optical fiber.

When probe 3 itself is inserted into the body or the organs of an animal, the resolution with which the internal conditions are formed into a picture image and observed depends on the number of optical fibers in image guide A and light guide B. Multiple strands of thin optical fibers are bundled together.

(C) Treatment of internal and external tissues by laser irradiation.

By irradiating the affected area with high output laser light (or microwaves), the external surface of the body is treated with applied heat. Irradiates with a certain wavelength, for example ultraviolet rays, in order to perform gene manipulation inside the cells.

(D) Photochemical reaction examination by laser irradiation.

Irradiates with laser light in order to cause a reaction in light reactive drugs condensed in the affected area.

(E) Liquid injection.

Performs the cleaning, sterilization, and supply of liquid medicine internally, externally, and to the tip surface of the probe. Concretely, washing fluid, normal saline, drugs, disinfectant, coating material, light reactive drugs, genes, etc. are injected through lumen (E) from the liquid supply unit 17. Because genes can be injected through the probe 3, transfection in which genes are introduced into cells in a living body rather than in a culture is possible.

(F) Liquid suction.

Lumen (F) suctions such things as discharges of waste washing liquid, and blood, secretions, waste matter, or metabolic product for examination. By driving the ultrasound transducer 21 connected to supply unit 17 at this time, living tissue can be satisfactorily suctioned by oscillating and agitating saline or a high water-content gel material injected into the affected area. After suctioning one part of the living tissue, saline or the like is injected. The suctioned living tissue is transported to the suction unit by sequentially injecting normal saline for an amount of time corresponding to the suction strength and the length of the probe 3.

In order to peel off or remove a tumor or the like after treating the external surface of the body with applied heat, said tumor is suctioned by lumen (F). In this case too, the affected area can be oscillated or agitated with ultrasonic waves.

(G) Bending the probe tip.

The objects for manipulation can be expanded by bending, moving, or tilting the surface of the tip by means of the operation guides. In this way, such processes as picture image observation, injection of medicine into the affected area, and removal of tumors can be more precisely performed.

(H) Internal examination with ultrasound waves.

Used for form examination with ultrasound waves, generally practiced. For examination by spectrophotoscope, in such situations as for example when particular cells such as introduced genes are penetrated by a designated amount of light at a certain wavelength, the amount of the particular cells inside the living organism can be evaluated.

(I) Electrodes.

Electrodes perform medical treatment on internal and external tissues when used for a living body monitor, current stimulation, current induction, and current discharge. Electrodes can also be used for electroporation in which genes are introduced inside cells by applying voltage, having injected the genes through lumen (E).

Figure 4:
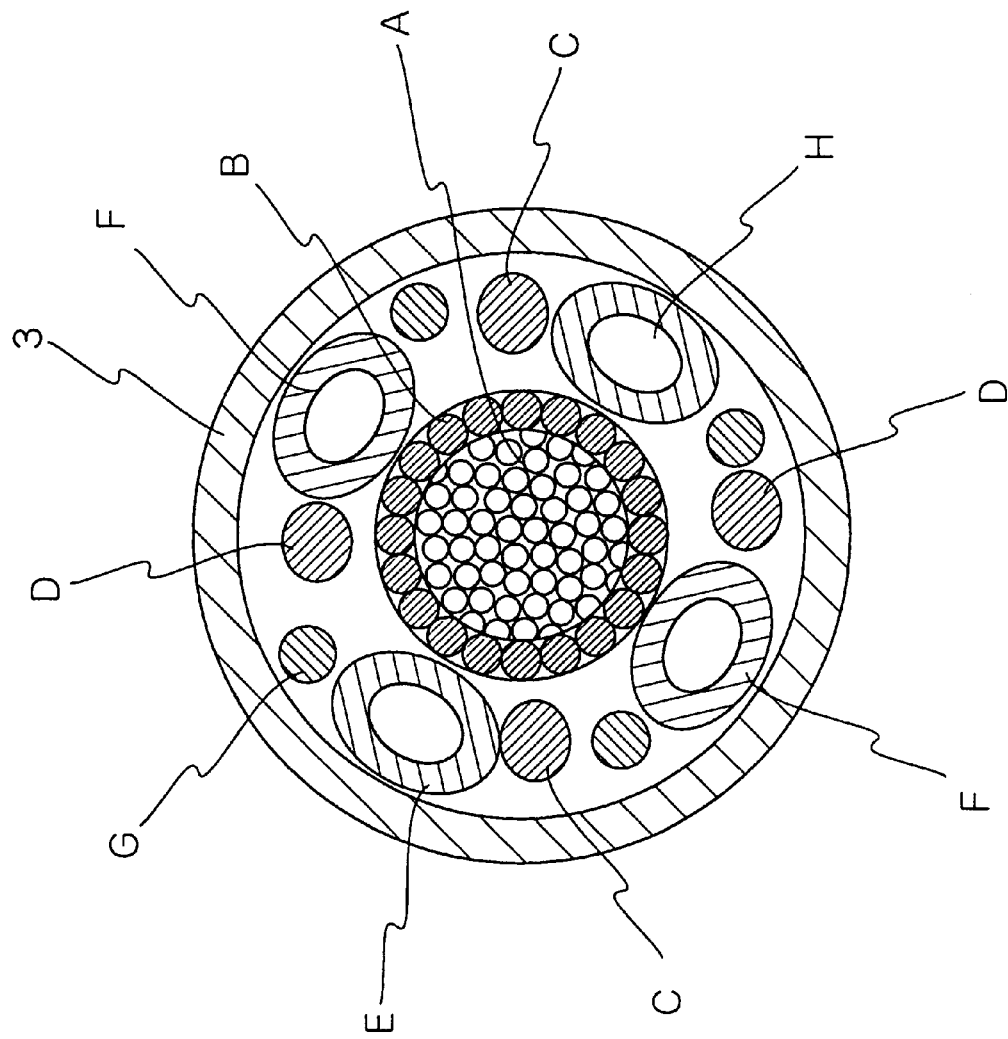
FIG. 4 is a sectional view showing a cross-section of the probe shown in FIG. 1.

Referring to FIG. 4, probe 3 is cylindrical, and all respective tubes are placed inside around the image guide A in the central position. The light guide B is placed so that it surrounds the periphery of the image guide A. Laser irradiation fibers C and D and liquid injector lumen E and liquid discharge lumen F are placed symmetrically around the center of the probe 3. In order not to shift the weight center of probe 3 from the central position of probe 3 by much, members with the same structure are placed symmetrically around the center of probe 3. In this way, the bend control is precise and the probe sending operation is stable.

Figure 5:
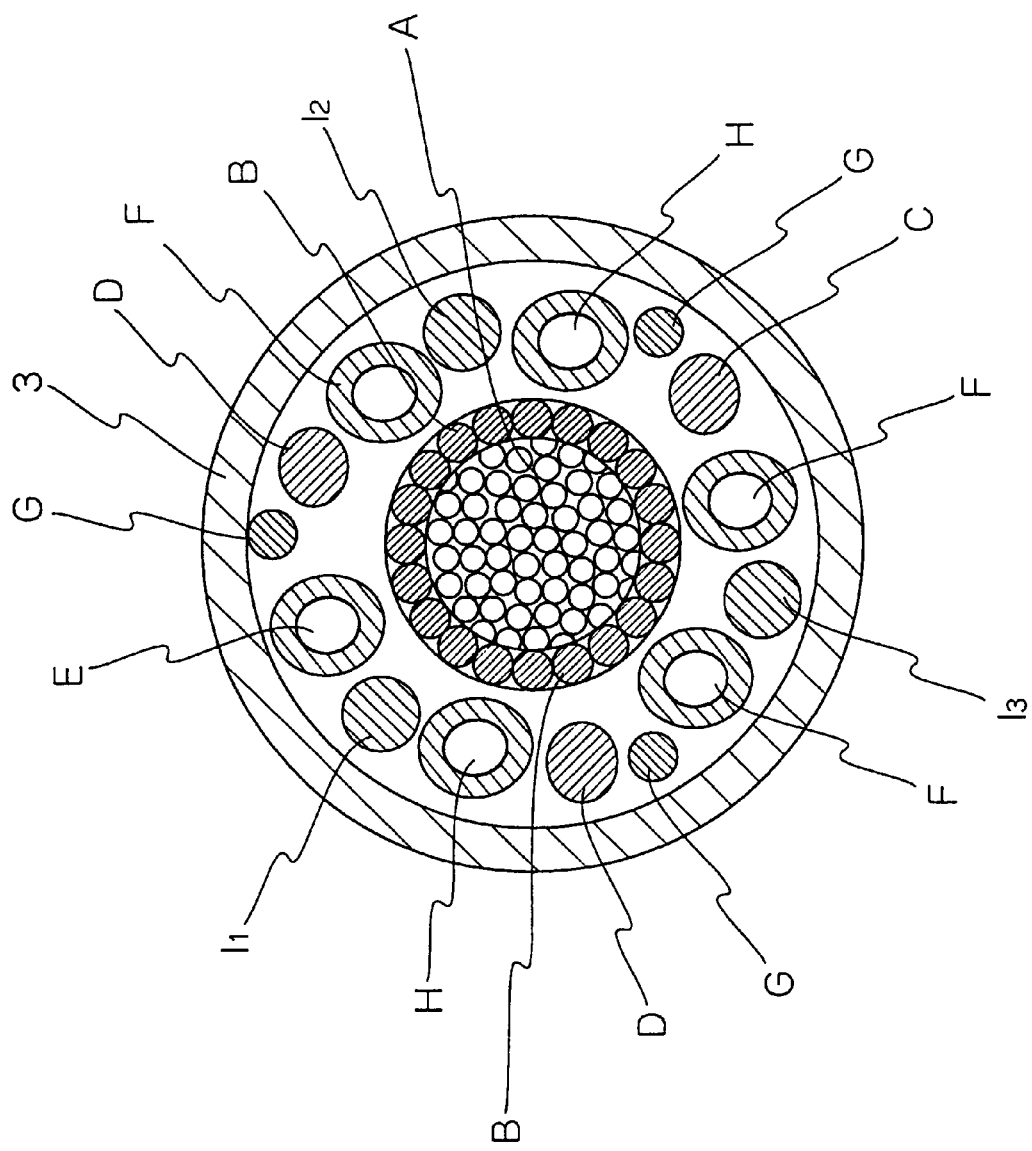
FIG. 5 is a sectional view showing a cross-section of the probe with three operation wires.

Referring to FIG. 5, probe 3 is encloses 6 lumens and 3 operation guides. FIG. 5 shows the center of weight in the center of the probe, as in FIG. 4, and the placement of three wires for control of the direction of the tip. Carbon electrodes (I1)–(I3) are similarly placed on the object. Carbon electrode I1 is a reference electrode, carbon electrode I2 is a cathode, and carbon electrode I3 is an anode. As shown in FIG. 5, when there are multiple lumens, the number of lumens for discharging liquid may be increased, or the number of lumens for injecting liquid may also be increased depending on the type of drug to be injected.

Figure 6:
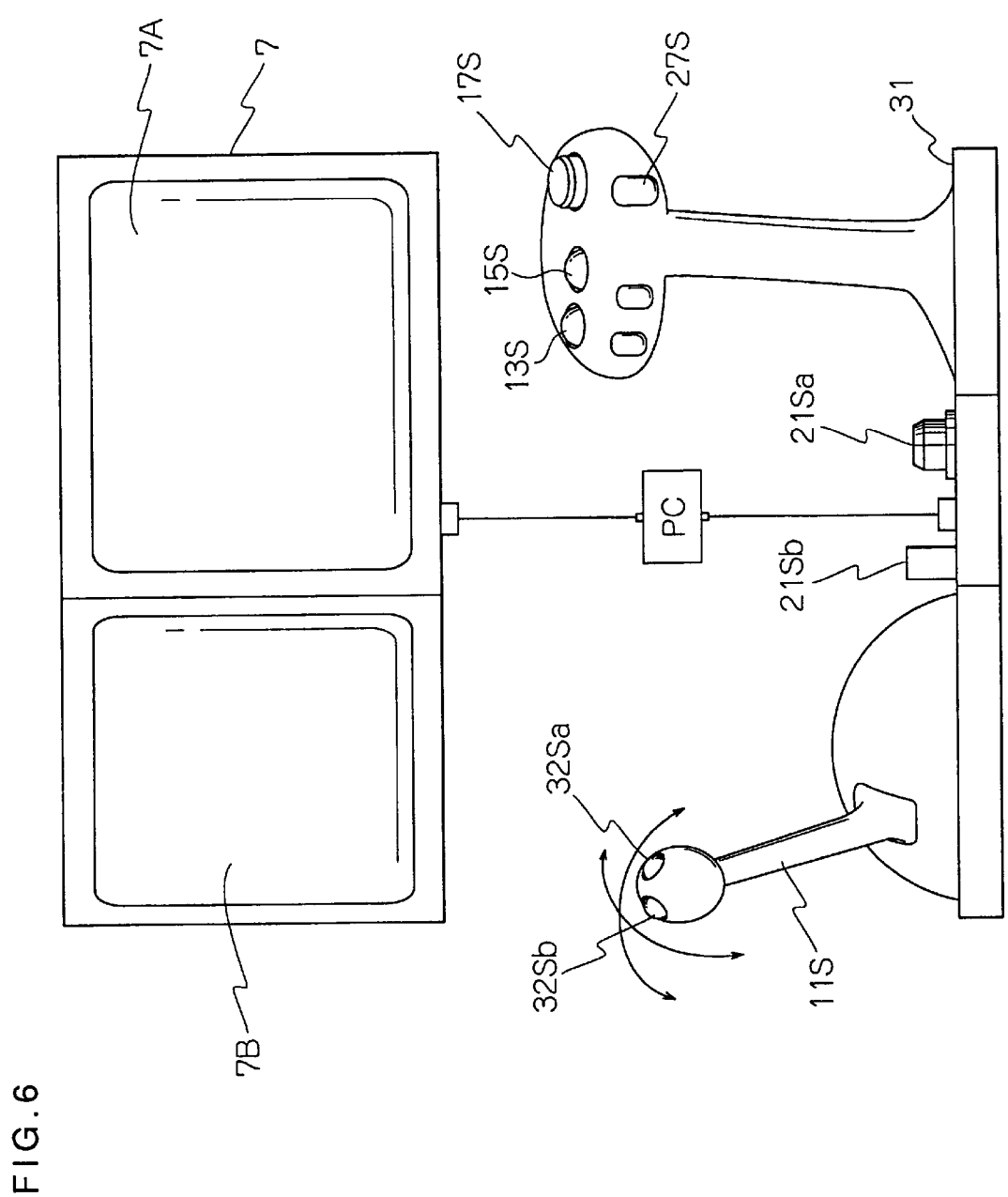
FIG. 6 is an explanatory view of a TV and one example of the input mechanism shown in FIG. 1.

Referring to FIG. 6, display 7 and one example of the input mechanism becomes clear. Here, all control functions connected to PC 29 can be operated using joystick 31. Besides a lever that controls the bending direction of the tip of the probe 3, transmission and control switches for all devices are also found on joystick 31.

Display 7 comprises region a 7A which displays a picture image photographed by the CCD camera 33, and region a 7B which displays an ultrasound image. In other words, display 7 can be divided into 2 or more picture images, and uses a monitor which can also switch the images. As a result it can display simultaneously an ultrasound image and a positioning picture image for laser irradiation, for example. Further, it can also display in region 7A simultaneously a picture image of normal tissue, and a picture image currently under observation.

An explanation of this operation example follows. If ultrasound wave generator button 21Sa is pressed when an ultrasound image is needed, the transmission of ultrasound waves begins. Then, for example if liquid supply switch 17S is pressed, the supply unit is activated, and liquid stored in advance in the liquid supply unit is injected into the affected area shown in display 7. Then for example when normal saline is injected in order to wash the affected area, if the liquid suction switch is pressed, the normal saline is suctioned.

Thus, the affected area becomes clear, and when performing laser light irradiation, laser irradiation switch 13S is pressed. The switch indicated by key 15S is a switch that causes the laser to irradiate in order to cause a light reaction. If the direction of the light is incorrect, operate bend control lever 11S. In response to the operation of the bend control lever, the tip of the probe bends and the picture image shown in display 7 changes accordingly. Because the central position of the picture image shown in the display is the location of the laser light irradiation, the probe 3 itself can be moved deeper or shallower as necessary by changing the bend angle with the bend control lever 11S. When positioning is finished, press down laser irradiation switch 13S. The change to the affected part by the laser irradiation is displayed on the display in realtime. While confirming the change to the affected area on the display, the treated affected area is suctioned by pressing the liquid suction switch after proper laser irradiation. A high water-content gel is supplied by the liquid supply switch, and by also pressing the ultrasound wave transmission switch 21Sb, the affected area is agitated making suction easy.

When manipulating the electrodes, it is best to make the laser irradiation switch into a switch that applies voltage to the electrode.

Referring again to FIG. 1, the corresponding parts of probe 3 and the system main body 2 are connected by the connection members 4. Accordingly, when the probe 3 is used on a certain examinee, these are removed for use of a new probe when using on another examinee. In other words, probe 3 becomes disposable. These connecting members 4 are plastic FC connectors, and are discarded along with probe 3 after use. Here, connecting members 4 are mounted on all of the structural elements contained in probe 3. Concretely, these are the optical system, the operation wire control system, the laser irradiation system, and the ultrasound wave system.

Instead of controlling each system independently with standard FC connectors, it is also possible to prepare a single unit, multi-channel joint connector specially designed for this system. Due to the single unit form, it is easy to prevent elementary errors such as forgetting to connect a system. Because all functions are held compositely as described above, they can be used in various situations regardless of the object of examination, and can be operated with a standardized method of use regardless of who is conducting the examination.

Figure 7A:
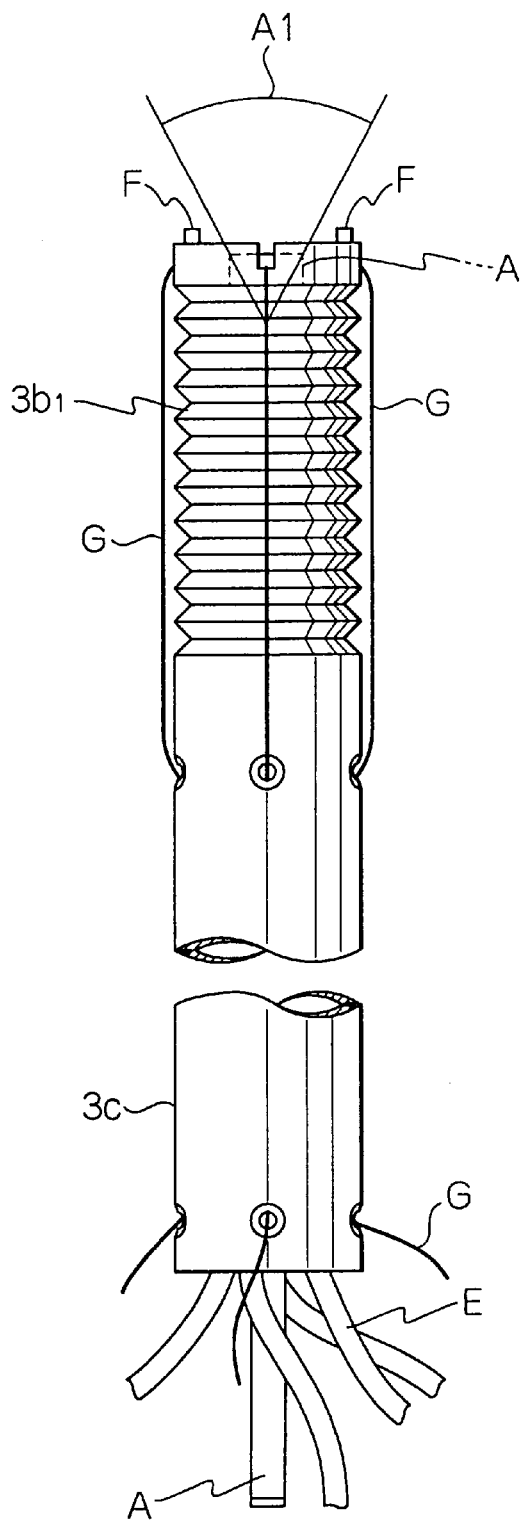
FIG. 7 is a frontal view showing the tip of the probe shown in FIG. 1: 7(A) shows it unbent; 7(B) shows it bent.
Figure 7B:
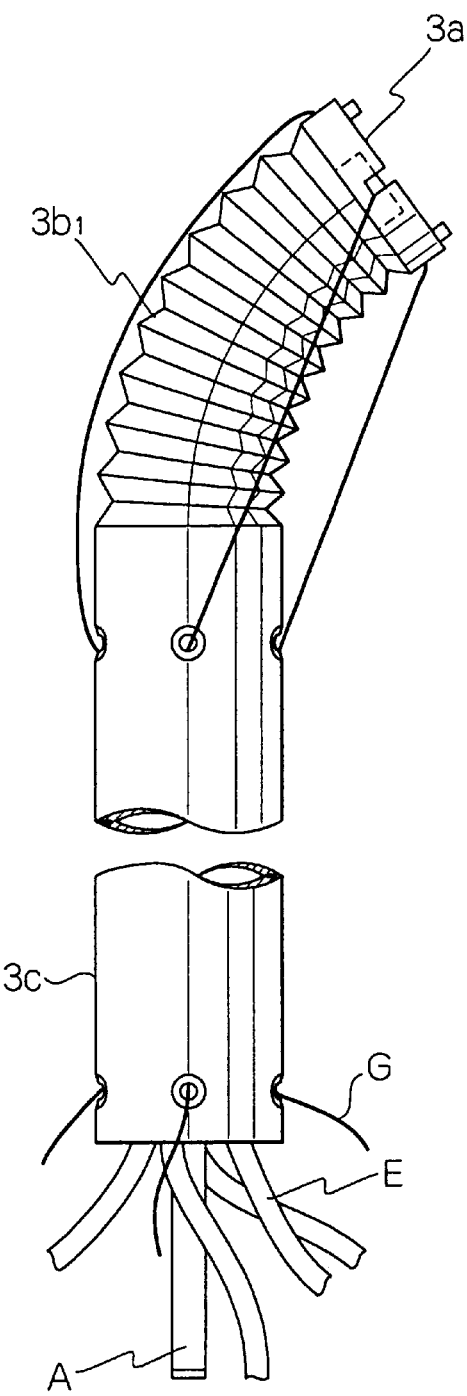

Referring to FIG. 7, a bending portion is mounted on the tip of the probe 3. Bending portion 3b1 is in the form of an accordion with notches cut into the probe 3. By making it in an accordion form, flexibility is added to the tip as shown in FIG. 7(B), and it can be easily bent. Thus, in the present invention, the bending portion 3b1 is bent by operation wires G which pull from the outer periphery of the tip. Operation wires G pass along the outer periphery of the probe 3 from the tip 3a of the bending portion to the rear end of the bending portion 3b1. Then they pass through the inner periphery of the probe from the rear end of bending portion 3b1 to the end of said probe 3.

The tip 3a houses the front ends of the image guide A and the light guide B installed inside the probe 3. A high-polymer, easily sterilized or incinerated material is used for the sides of the probe, so no special disposal process is necessary.

Four operation wires G are affixed to the tip of the probe 3 on the outer periphery of the tip at uniform intervals. The operation wires G are placed on the tip 3a of probe 3, and by applying tension to any one of these operation wires G, the probe 3 will bend to the side of the operation wire G to which the tension was applied. Concretely, a fiber of high polymer material such as a high-strength, high-elasticity engineering plastic typified by polyamide, polyimide or a high-density polyethylene, or a composite fiber containing these is used for the operation wires G. A Kevlar family material is a good high polymer material.

Prescribed notches are built into the tip 3a of the probe 3 corresponding to each operation wire G. These notches are created for the purpose of fixing prescribed positions for the operation wires G. In other words, four notches at 90E intervals are formed in the cross-section of the cylindrical probe 3, operation wires G pass through these notches, and the tips of operation wires G are affixed inside probe 3. A pre-cast mold may be used when casting the probe to form these notches, or as the processing is precise and the material of the members is a polymer material with good workability, they may also be formed afterwards by laser processing or electric discharge processing.

The operation wires G are housed inside probe 3 on the side of the system main body 2, but they are extended outside at one point near the tip of probe 3. Then, following the outer periphery of probe 3, they pass through the above notches, and arrive back inside the probe 3. In the present embodiment, 4 operation wires G are used, but the number of operation wires G is not particularly limited. In other words if the tip of probe 3 is constructed such that it will bend in a single direction decided in advance and an operation wire G is mounted in a position which could return the tip to a straight line, one could freely control the bending of the tip of probe 3 even with only one operation wire G.

Figure 8:
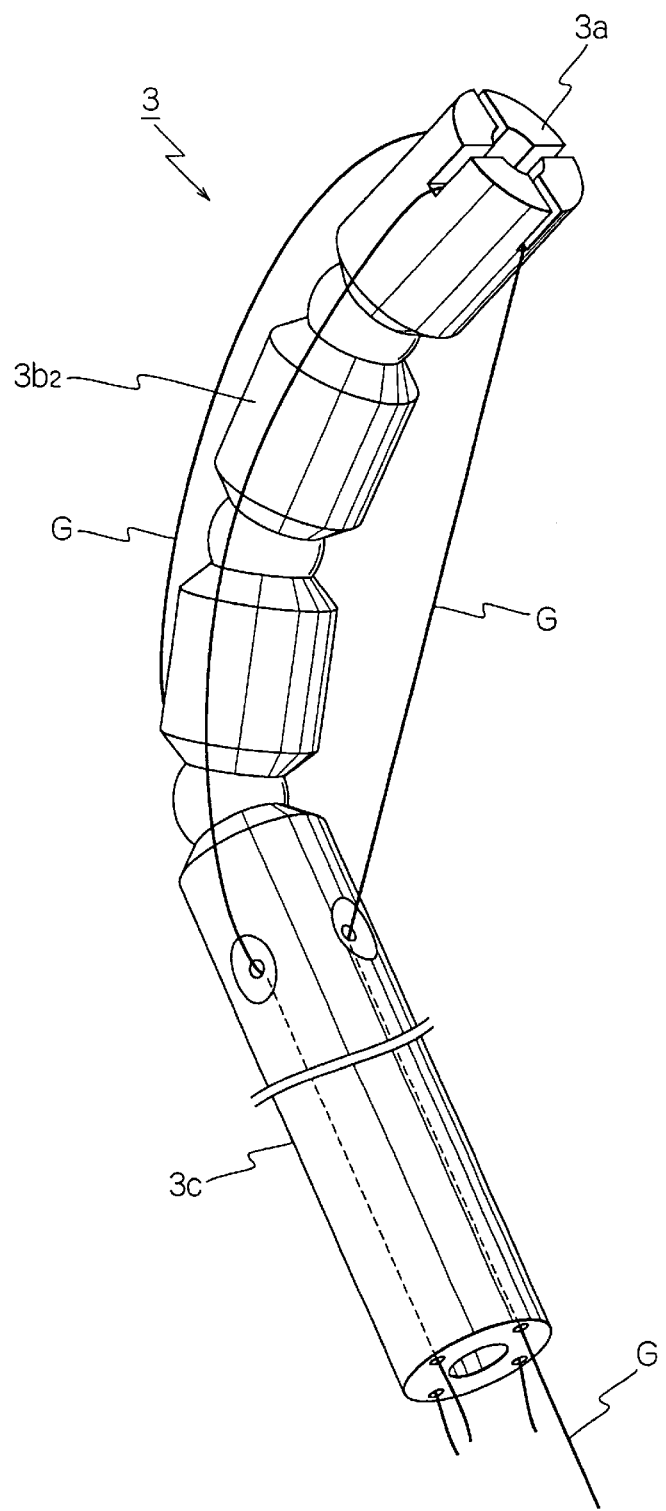
FIG. 8 is an oblique view of an example in which joints are used for the bending portion.

Referring to FIG. 8, tip 3b2 with joints is used instead of the tip 3b1 with an accordion shape shown in FIG. 7. Joints 3b allow each member comprising the tip of probe 3 to bend together and allow the direction in which probe 3 bends to change flexibly. In the example shown in FIG. 8, two joints 3b are located between the tip 3a and the side member 3c of the system main body 2, and allow sufficient bend angle to be achieved. However, one joint 3b is also acceptable, or three or more are also acceptable.

Figure 9A:
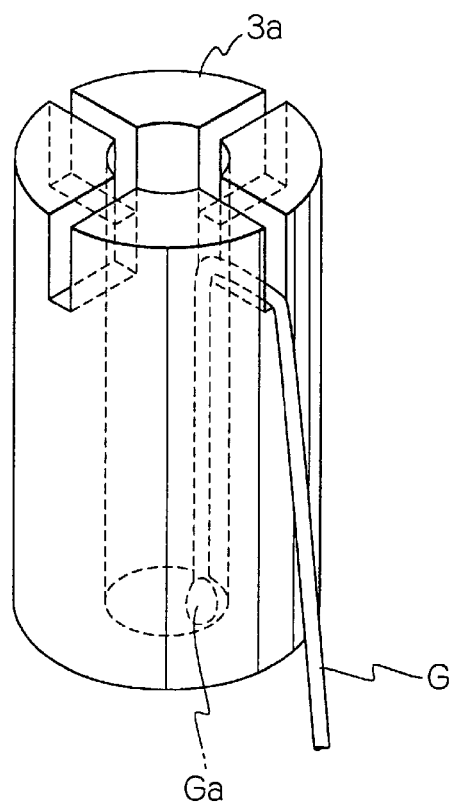
FIG. 9 shows one example of the tip of the bending portion: 9(A) shows the tip with operation wires affixed internally; 9(B) shows the operation wires attached to themselves on the outer periphery.
Figure 9B:
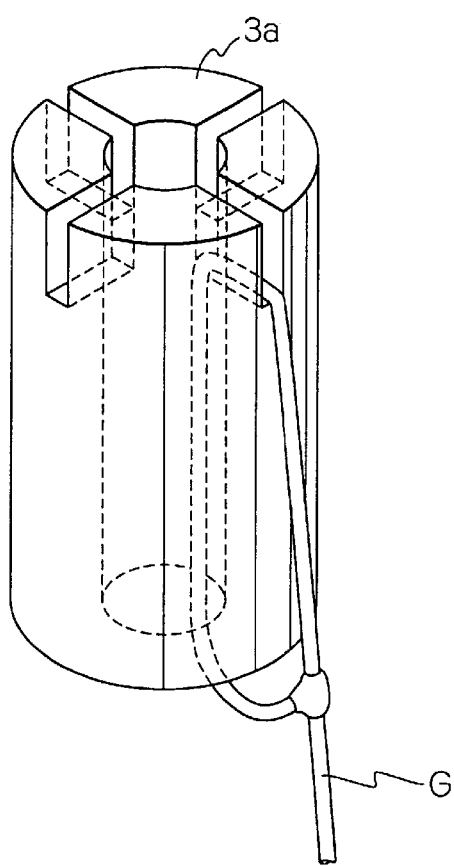

Referring to FIG. 9, there are two methods of affixing the operation wires: as shown in FIG. 9(A) they are attached to the inside of probe 3; and as shown in FIG. 9(B) they are constructed such that the tips of operation wires G extend outside of probe 3 and are re-joined to themselves. In the example shown in FIG. 9(A), spot melt-deposition or cold heat welding by light irradiation with optical fibers and a photo hardened resin varnish are suitable for the actual attachment of the wires G.

Referring to FIGS. 7 through 9 again, a convex lens made from decomposable plastic can be attached as an accessory on the tip of the image guide, to allow a wider range of observation of the observation object. When the convex lens is attached, the field of vision of the image guide becomes 120E, and so when processing the picture image, it is best to flatten out the curved observation surface. Also, by spreading the sides of the probe with a hydrophilic polymer membrane and immersing it in a liquid such as normal saline slightly before use, friction between the surface of the probe and the surface of mucous membranes inside the body or the like can be reduced. Further, if a thin membrane tube is mounted between the inner peripheral surface of the probe and the multiple tubes, distortion of the multiple tubes through bending is reduced. For example, if the tips of multiple tubes (A)–(I) are affixed to the tip of the probe as shown in FIG. 7(A), the tubes which need to stretch due to the bending pull the tubes placed at the rear end of the probe. At this time, the parts bent along with the bend of the probe 3, move inside the probe without friction due to the thin membrane. If the thin membrane is extended to the straight portion of the probe, because the force that moves each tube toward the tip is transmitted in a straight line, the tubes stretch and changes in the shape of the tubes is restricted to a minimum.

Referring to FIG. 7(A), the field of vision of image guide (A) is approximately 60E. As a result, even if tubes to the inside and outside of a tube placed inside the probe is extended further than the tip 3a of the probe, it will not hinder the photographing range of the image guide. For this reason, for example if a lumen that performs suctioning is extended from the tip 3a slightly, suctioning is made easy. Electrodes (I) can also be extended.

Figure 10A:
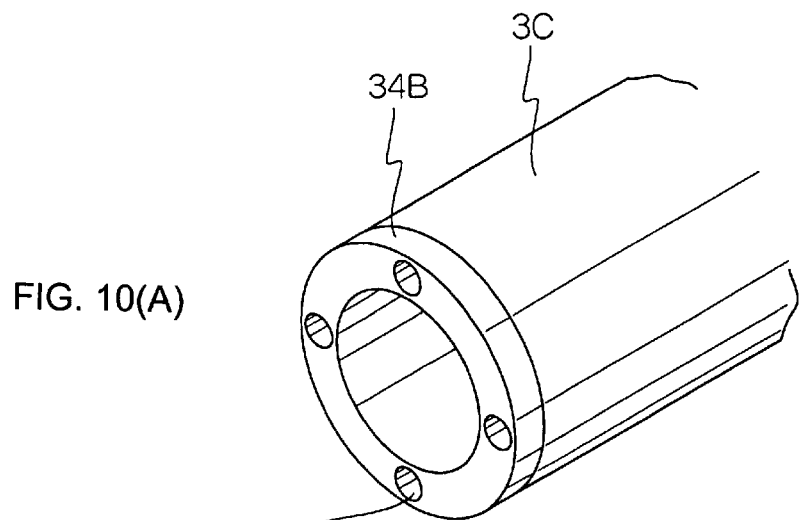
FIG. 10 is an oblique view showing one example of the rear end of the probe: 10(A) shows an example with a reinforcing member attached; 10(B) shows an example with exit holes built into the side of the probe; 10(C) shows an example with guide rings built onto the rear end of the probe.
Figure 10B:
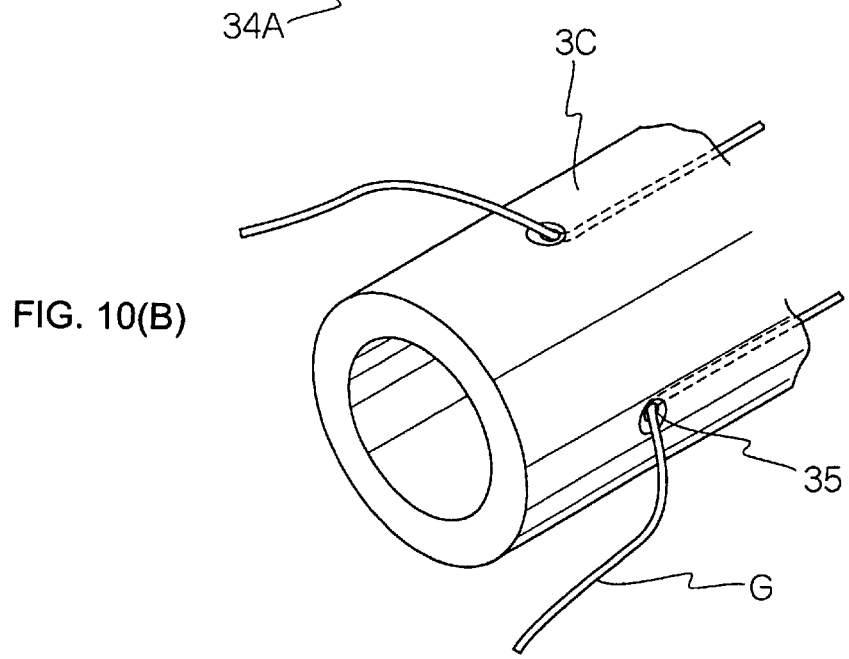
Figure 10C:
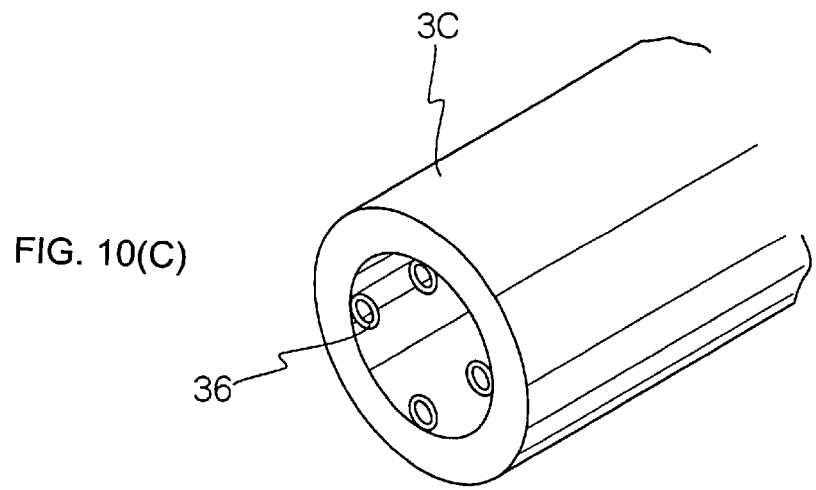

As shown in FIG. 10, it is easiest to set position and control tension when only bending wires G are independent and branched at the base of probe 3. When wires G exit from 3a and enter 3c as shown in FIG. 4, guide holes 34A can be built inside 3c as members that connect the base of the probe to the driving portion as shown in FIG. 10(A). In this case, reinforcing member 34B made of a material even stronger than the material of the probe is attached to the rear end of the probe. If wires G exit a second time from the rear end 3c of the probe, exit holes 35 as shown in FIG. 10(B) are constructed, or guide rings 36 are built into the base as shown in FIG. 10(C), making control from the driving system easy.

If these guides are not constructed, problems with the control of tension, such as wires G becoming entangled with a member inside 3c, arise easily. Through-holes to the inside of 3c in FIG. 10(A) are opened at decided degree intervals by perforation with extremely thin heat wires or by laser perforation before the probe is assembled.

Because considerable friction is applied to the members on the side of the probe, though for a short period of time, some form of reinforcement should be applied to the entry/exit holes for wires G such as a lubricant coating or abrasion resistant seal, tape, or padding.

Referring to FIG. 11, instead of the construction shown in FIG. 10, forked foot 37 separates the operation guides G. Forked foot 37 comprises attaching member 37A to which the end 3c of probe 3 is attached, legs 37B extended from the end of attaching member 37A pointing outside of the circumference of probe 3, and guide holes 37C built inside legs 37B through which operation wires G enclosed in the probe and mounted inside the legs 37B are guided from attaching member 37A to the outside of legs 37B. A sealing material shown by key 11E can be used to fix the forked foot to the rear end of the probe.

Figure 11A:
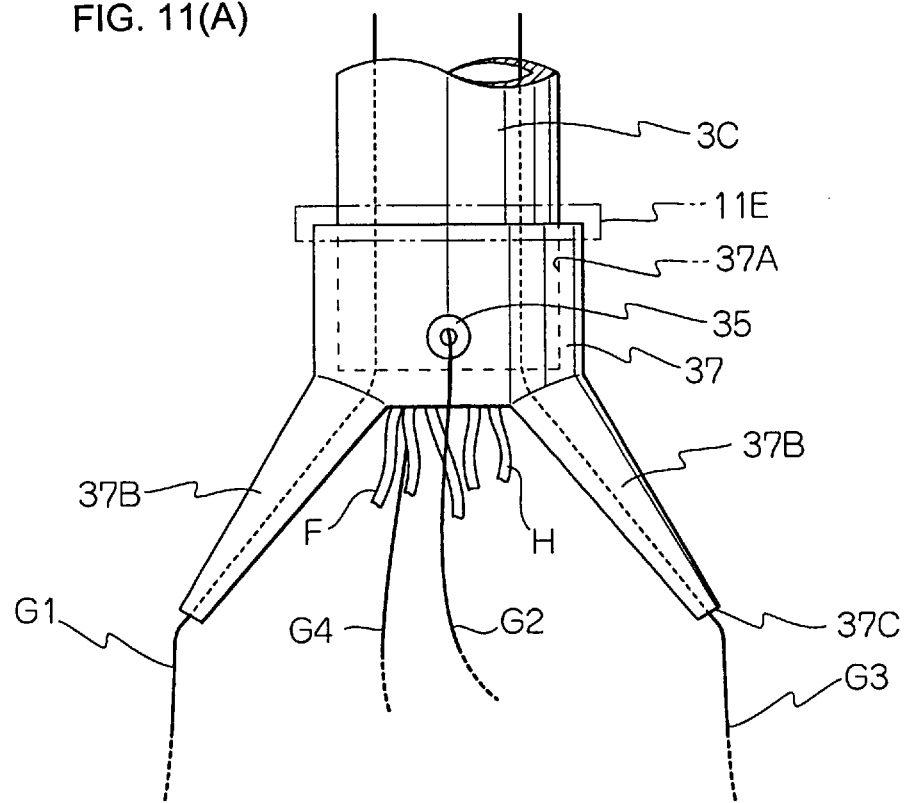
FIG. 11 is a frontal view showing one example of a forked foot that guides the guides and is connected to the rear end of the probe: 11(A) shows an example with two feet; 11(B) shows an example with three feet.
Figure 11B:
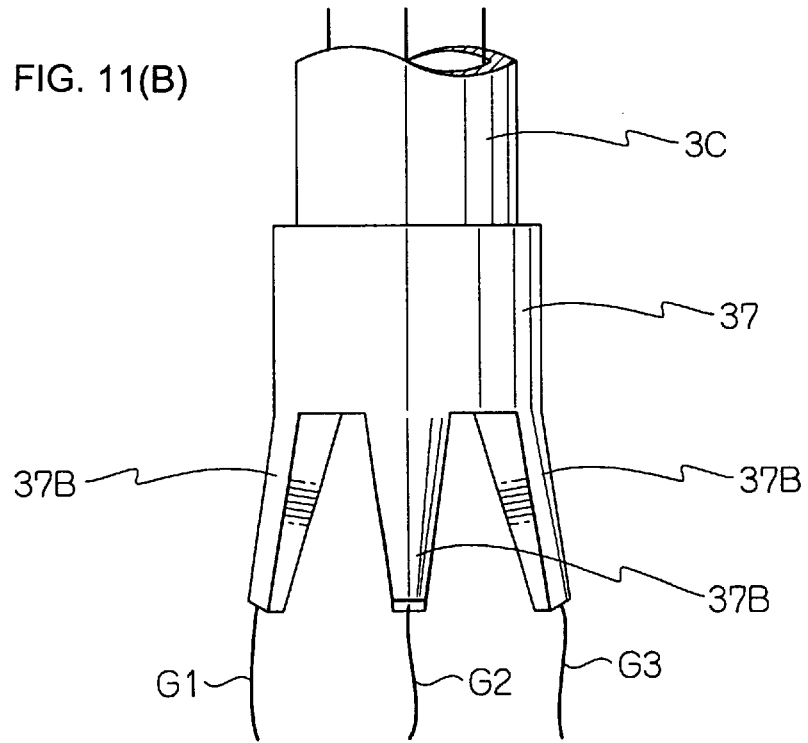

By using this sort of special guiding member the probe can be easily detached. FIG. 11(A) shows four operation guides, but FIG. 11(B) shows an example of the forked foot with three operation guides, corresponding to FIG. 5.

Figure 12:
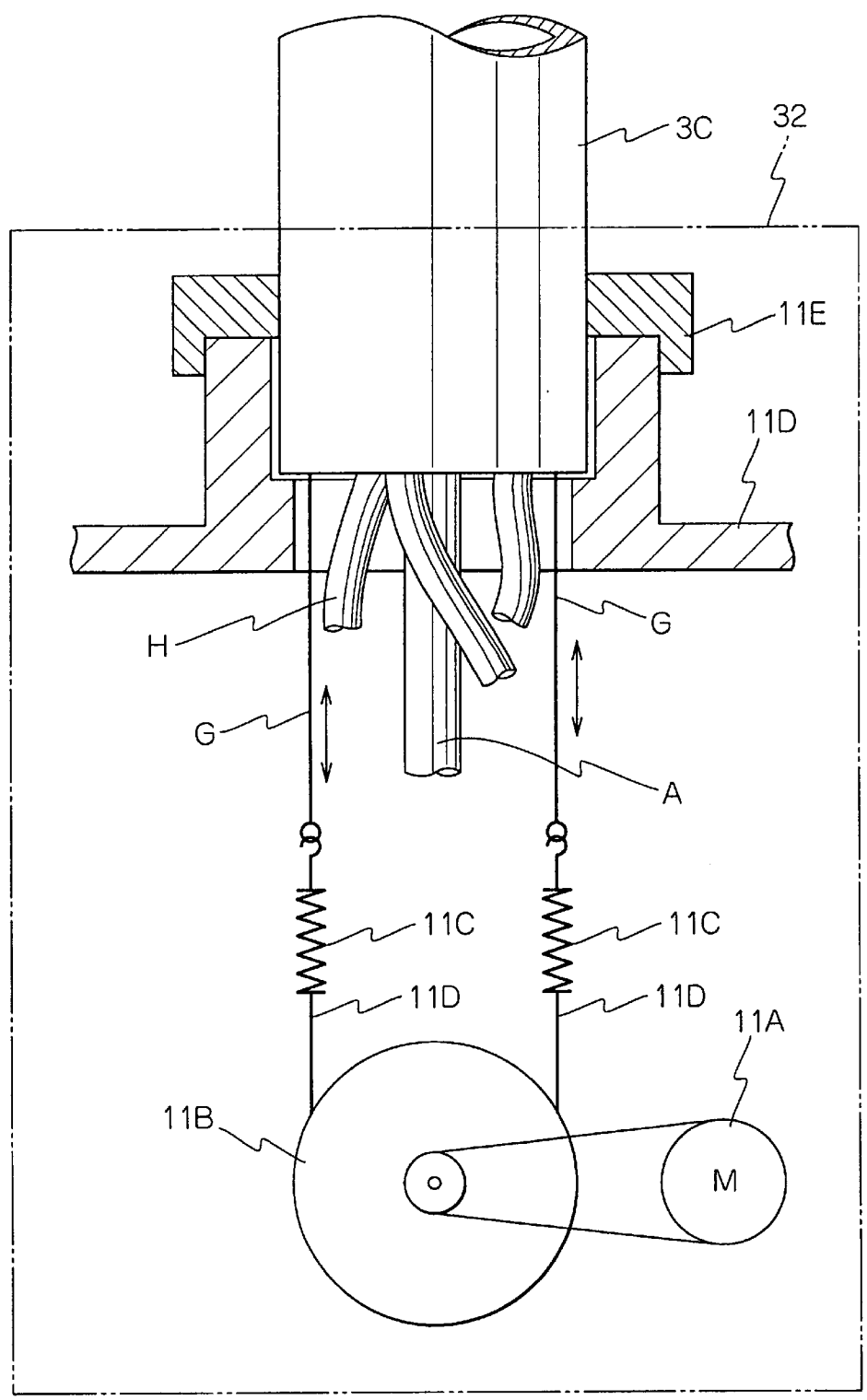
FIG. 12 is an explanatory view showing one example of the driving mechanism of the tip of the probe shown in FIG. 1.

Referring to FIG. 12, the operation wire driving mechanism, or in other words tip driving mechanism 11, comprises driving wires 11D having springs 11C detachably attached to the operation wires, roller 11B that winds up or sends out the operation wires, and motor 11A which rotates roller 11B in response to the operation of input mechanism 31. The motor shown by key 11A rotates roller 11B, first pulling then pushing springs 11C. As a result, play is generated in the operation of the tip, and errors caused by rapid operation, such as when lever 11S hits an object, are prevented. By mounting springs 11C, in the event that tip 3a of the probe hits against something, springs 11C stretch so as not to injure the object. In the example shown in FIG. 12, one roller and gear are used for two guides, but they can also be controlled one at a time.

Figure 13:
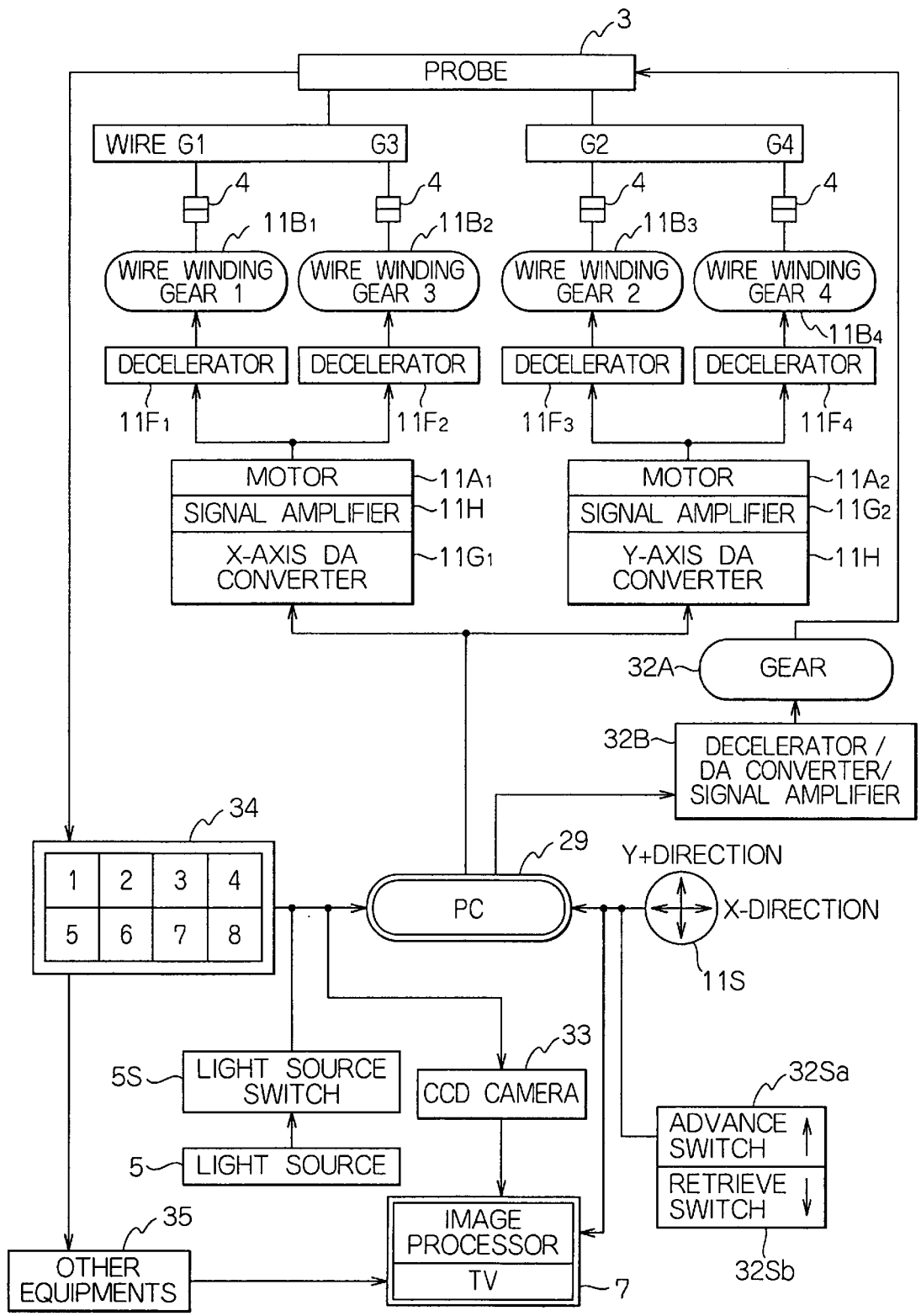
FIG. 13 is a block diagram showing the construction of the control system with four operation wires.
Figure 14:
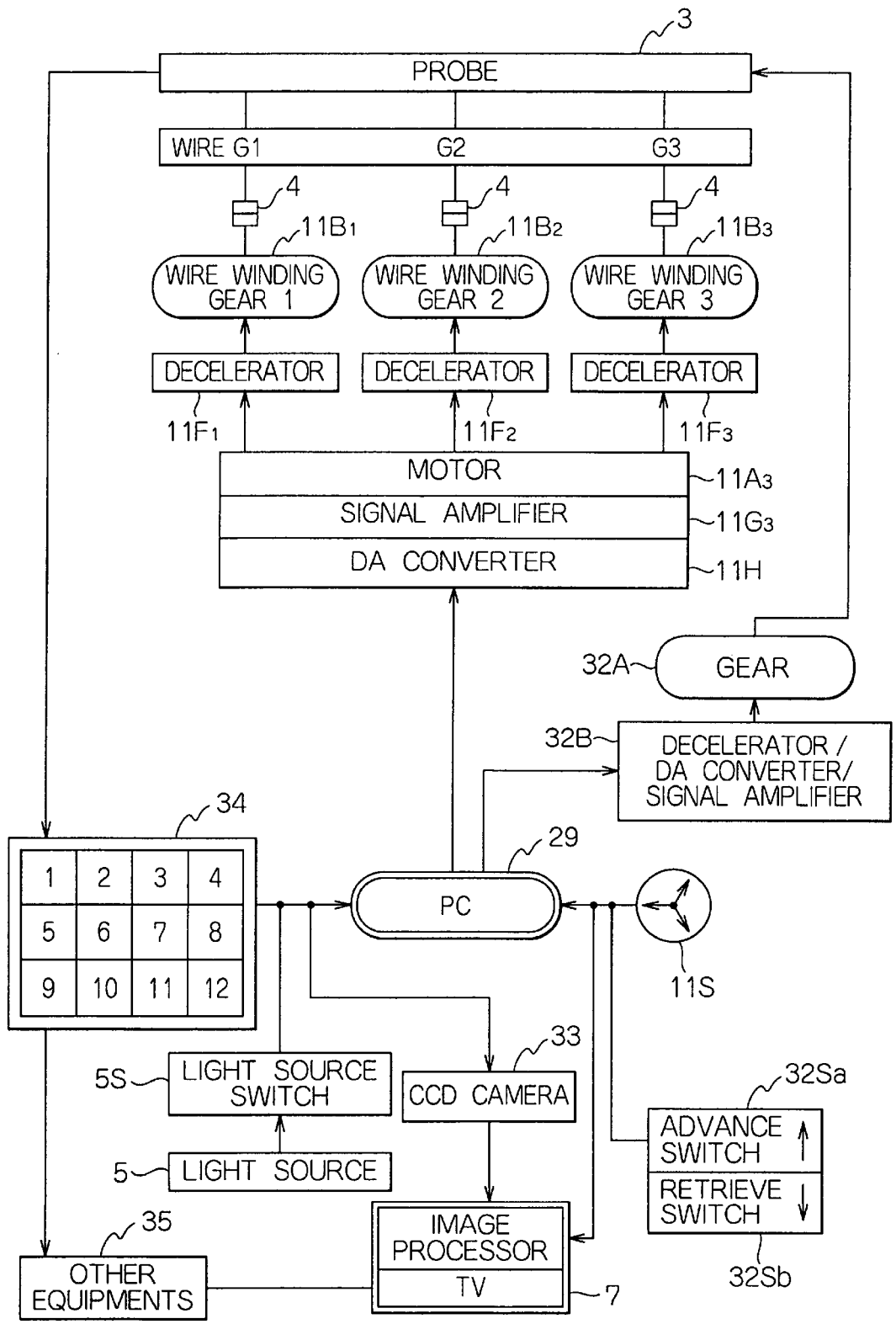
FIG. 14 is a block diagram showing the construction of the control system with three operation wires.

Referring to FIG. 13, an example is shown in which four wire winding gears 11B1–11B4 are used for four wires. In this case, when bend control lever 11S on the joystick is operated, a signal indicating the operational direction and size corresponding to this operation is output to PC 29. In PC 29, a signal that drives motors 11A1-11A4 is output in response to the signal output from bend control lever 11S. When using a stepping motor as motor 11A, it outputs a number of pulses corresponding to the rotation angle. Further, when using a motor with analog drive, it is equipped with a D/A converter 11G that converts the output from PC 29 to an analog signal, a signal amplifier 11H that amplifies the signal output from D/A converter 11G, and a motor that transmits the rotation strength to decelerator 11F according to a signal output from the signal amplifier. Referring again to FIG. 11(A), operation wires G1 and G3, and operation wires G2 and G4 are opposite each other. As a result, in the example shown in FIG. 13, the direction control signal equivalent to the X axis of the joystick is converted by a single D/A converter for the pair of wires G1 and G3. On the other hand, in the example shown in FIG. 14, because there are three operation wires corresponding to FIG. 11(B), PC 29 outputs a signal equivalent to axes 0E, 120E, and 240E from the center of the joystick to D/A converter 11G3.

Channel 34 in FIGS. 12 and 13 switches control systems: for example it switches such things as a signal that is output directly to the TV and a signal that is output once to the PC.

Figure 15:
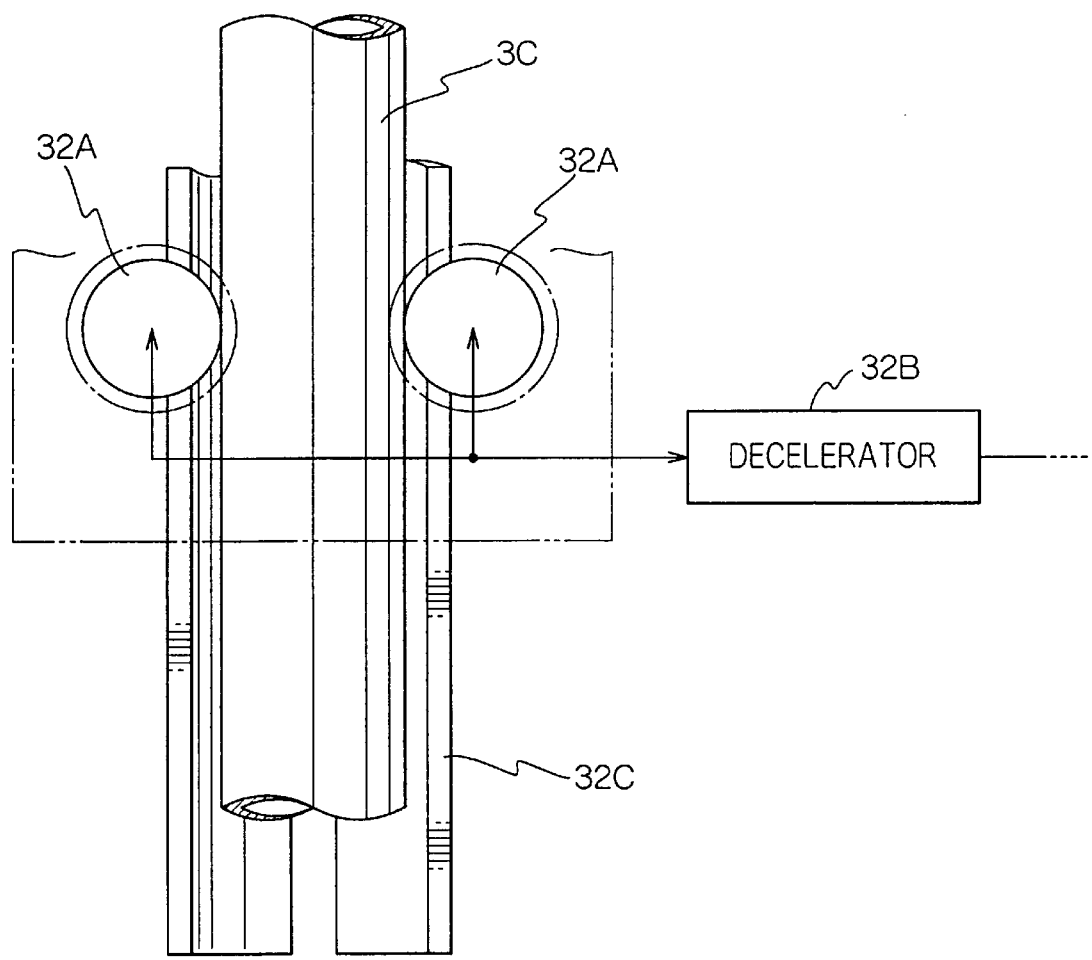
FIG. 15 is a planar view showing the construction of the sending mechanism that sends the probe backward and forward.
Figure 16:
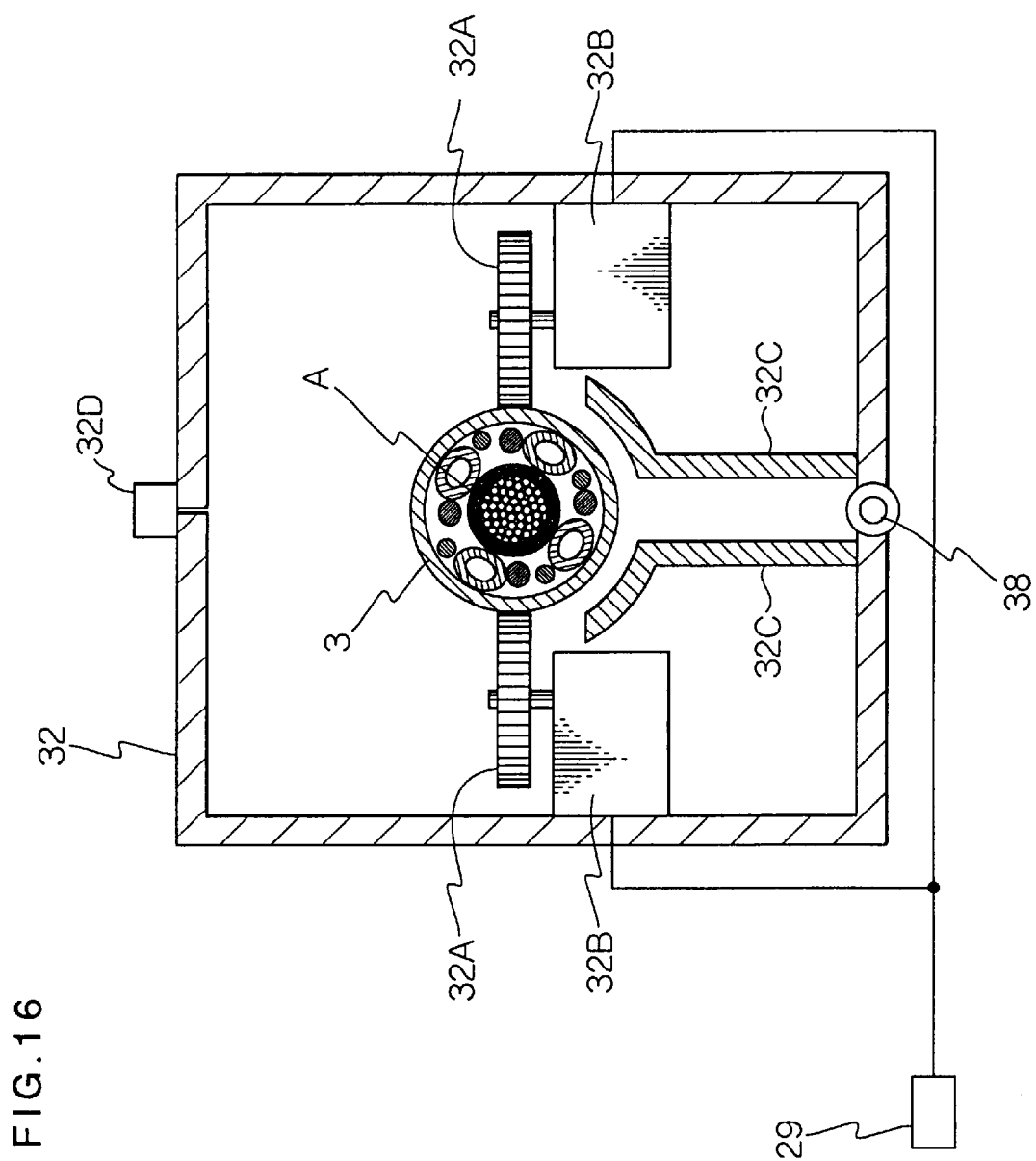
FIG. 16 is a sectional view of the sending mechanism shown in FIG. 15.
Figure 17:
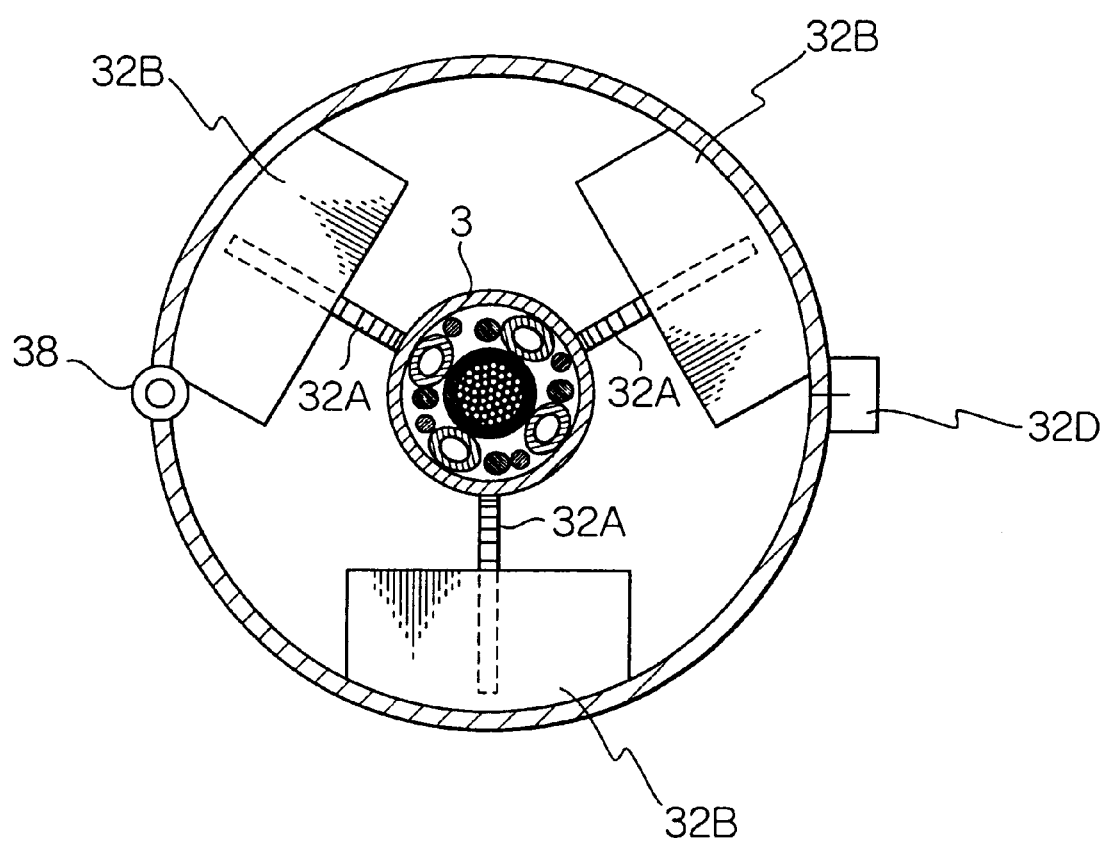
FIG. 17 is a sectional view showing an example of the sending mechanism with three gears.

Referring to FIG. 15, the sending mechanism comprises two gears 32A and 32A and 32B which is a decelerator, a motor, or the like. Of the two gears 32A and 32A, one should be a driving gear and the other should be a following gear. Because the side of probe 3 is flexible and is a high-polymer material, the teeth of gears 32A bite into the side of the probe. As a result, when gears 32A are rotated, the probe advances or retreats in response to the rotation. FIG. 16 is a sectional view of this sending mechanism. In the example shown in FIG. 15, because there are two gears 32A, guide 32C that guides the sending operation of cylindrical probe 3 is mounted. The decelerator 32B is housed inside gear box 32B shown in FIG. 16. The sending mechanism cover opens and closes by hinge 38 and switch 32D so that gears 32A bite into the side of probe 3. FIG. 17 shows a construction with three gears 32A. When there are three gears, probe 3 can be satisfactorily sent out without any special guiding members.

The examples shown in FIGS. 15 through 17 only show members that advance the probe forward and backward, but as shown in FIG. 12, the tip driving mechanism 11 as a single unit with probe 3 is sent by sending mechanism 32.

What is claimed:

1. A hybrid operation system for manipulating an object upon insertion of a tip of a conduit into the object, comprising:
    a conduit having multiple tubes therein, wherein a distal end portion of said conduit is flexible and wherein said conduit has at least one opening defined therein prior to said distal end portion;
    a drive mechanism that drives said multiple tubes within said conduit;
    an input mechanism that is responsive to an operator to output commands to said drive mechanism to control an operation of said multiple tubes;
    a plurality of notches defined in a tip of said distal end portion of said conduit;
    a plurality of operation wires extending from within said conduit to an outside of said conduit through said at least one opening in said conduit, wherein each of said plurality of operation wires further extends from said at least one opening through a corresponding one of said plurality of notches to an inner periphery of said conduit;
    a tip drive mechanism that adjusts respective tensions of said plurality of operation wires to bend said distal end portion of said conduit.

2. The system of claim 1, wherein said plurality of operation wires are affixed to an inner side of said distal end portion.

3. The system of claim 2, wherein said plurality of operation wires and the inner side of said distal end portion are attached to each other by a photo hardened resin.

4. A hybrid operation system for manipulating an object upon insertion of a tip of a conduit into the object, comprising:
    a conduit having multiple tubes therein, wherein a distal end portion of said conduit is flexible and wherein said conduit has at least one opening defined therein prior to said distal end portion;
    a drive mechanism that drives said multiple tubes within said conduit;
    an input mechanism that is responsive to an operator to output commands to said drive mechanism to control an operation of said multiple tubes;
    a plurality of operation wires extending from within said conduit to an outside of said conduit through said at least one opening in said conduit, wherein each of said plurality of operation wires further extends from said at least one opening to an inner periphery of said distal end portion of as conduit;
    a tip drive mechanism that adjusts respective tensions of said plurality of operation wires to bend said distal end portion of said conduit; and
    a forked foot portion comprising (a) an attachment member that is attached to a proximal end of said conduit, (b) a plurality of leg members extending from said attachment member, and (c) a plurality of guide holes respectively defined within said plurality of leg members, said plurality of guides holes containing a respective one of said plurality of operation wires.

5. A hybrid operation system for manipulating an object upon insertion of a tip of a conduit into the object, comprising:
    a conduit having multiple tubes therein, wherein a distal end portion of said conduit is flexible and wherein said conduit has at least one opening defined therein prior to said distal end portion;
    a drive mechanism that drives said multiple tubes within said conduit;
    an input mechanism that is responsive to an operator to output commands to said drive mechanism to control an operation of said multiple tubes;
    a plurality of operation wires extending from within said conduit to an outside of said conduit through said at least one opening in said conduit, wherein each of said plurality of operation wires further extends from said at least one opening to an inner periphery of said distal end portion of as conduit; and a tip drive mechanism that adjusts respective tensions of said plurality of operation wires to bend said distal end portion of said conduit;

wherein said tip drive mechanism comprises (a) a plurality of drive wires, each having a spring along a length thereof, detachably connected to a respective one of said plurality of operation wires, (b) a roller having said drive wires wound thereon, and (c) a motor that rotates said roller in response to a signal input thereto.

6. The system of claim 5, wherein the send mechanism comprises multiple gears that bite into an outer surface of the conduit, and a motor that drives said multiple gears.

7. A hybrid operation system for manipulating an object upon insertion of a tip of a conduit into the object, comprising:

a conduit having multiple tubes therein, wherein a distal end portion of said conduit is flexible and wherein said conduit has at least one opening defined therein prior to said distal end portion;

a drive mechanism that drives said multiple tubes within said conduit;

an input mechanism that is responsive to an operator to output commands to said drive mechanism to control an operation of said multiple tubes;

a plurality of operation wires extending from within said conduit to an outside of said conduit through said at least one opening in said conduit, wherein each of said plurality of operation wires further extends from said at least one opening to an inner periphery of said distal end portion of as conduit;

a tip drive mechanism that adjusts respective tensions of said plurality of operation wires to bend said distal end portion of said conduit; and a send mechanism that advances and retracts said conduit within the object.

* * * * *